(12) United States Patent
Vrancken Peeters

(10) Patent No.: US 9,931,113 B2
(45) Date of Patent: Apr. 3, 2018

(54) NEEDLE-SUTURE COMBINATION

(71) Applicant: MELLON MEDICAL B.V., Nijmegen (NL)

(72) Inventor: Mark-Paul Franciscus Maria Vrancken Peeters, Nijmegen (NL)

(73) Assignee: MELLON MEDICAL B.V., Nijmegen (NL)

( * ) Notice: Subject to any disclaimer, the term of this patent is extended or adjusted under 35 U.S.C. 154(b) by 0 days.

(21) Appl. No.: 15/307,918

(22) PCT Filed: Apr. 29, 2015

(86) PCT No.: PCT/NL2015/050288
§ 371 (c)(1),
(2) Date: Oct. 31, 2016

(87) PCT Pub. No.: WO2015/167331
PCT Pub. Date: Nov. 5, 2015

(65) Prior Publication Data
US 2017/0055979 A1    Mar. 2, 2017

(30) Foreign Application Priority Data

May 1, 2014   (NL) .................................... 2012735

(51) Int. Cl.
*A61B 17/06* (2006.01)

(52) U.S. Cl.
CPC .. *A61B 17/06004* (2013.01); *A61B 2017/061* (2013.01); *A61B 2017/0609* (2013.01); *A61B 2017/06047* (2013.01)

(58) Field of Classification Search
CPC .... A61B 17/06004; A61B 2017/06019; A61B 2017/06023; A61B 2017/06047
See application file for complete search history.

(56) References Cited

U.S. PATENT DOCUMENTS 5,569,301 A * 10/1996 Granger ............. A61B 17/0469
606/223
5,667,528 A * 9/1997 Colligan .......... A61B 17/06004
606/224
5,865,836 A * 2/1999 Miller .................... A61B 17/06
606/222

(Continued)

FOREIGN PATENT DOCUMENTS

WO       2 108 319 A1    10/2009
WO    WO 2010/054433 A1   5/2010
WO    WO 2013/032329 A1   3/2013

*Primary Examiner* — Sarah W Aleman
(74) *Attorney, Agent, or Firm* — Birch, Stewart, Kolasch & Birch, LLP

(57) ABSTRACT

A needle-suture combination includes a surgical needle having two ends and a suture connection location arranged between the two ends; a suture; and a connection part. A first end of the connection part is connected to the needle at the suture connection location and an opposite second end of the connection part is connected to the suture. The connection part includes a connection part cross section area and the suture includes a suture cross section area. The connection part cross section area is smaller than the suture cross section area. The connection part has a length which is larger than a longest distance from the suture connection location to each of the two ends of the needle.

19 Claims, 5 Drawing Sheets

(56) References Cited

U.S. PATENT DOCUMENTS

| | | | |
|---|---|---|---|
| 6,056,771 A * | 5/2000 | Proto ................. | A61B 17/0469 606/222 |
| 2006/0253126 A1 | 11/2006 | Bjerken et al. | |
| 2010/0228270 A1* | 9/2010 | Bogart ............... | A61B 17/0469 606/144 |
| 2011/0282385 A1* | 11/2011 | Gilson ............. | A61B 17/06066 606/224 |

* cited by examiner

Figure 3a (A-A)
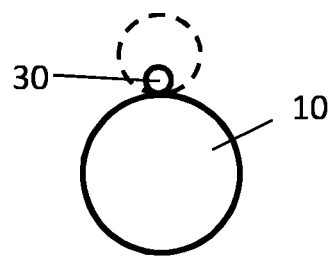
Figure 3b
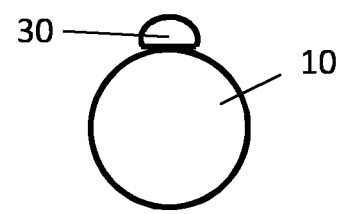
Figure 3c
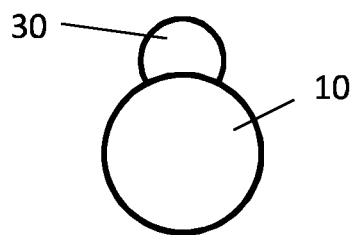
Figure 3d (B-B)
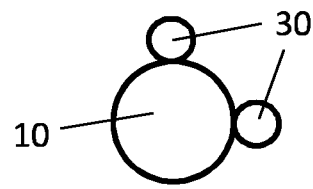
Figure 3e (C-C)
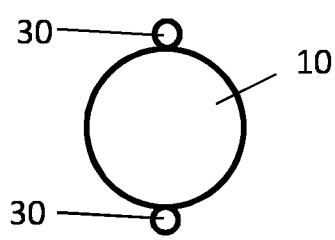
Figure 3f (D-D)
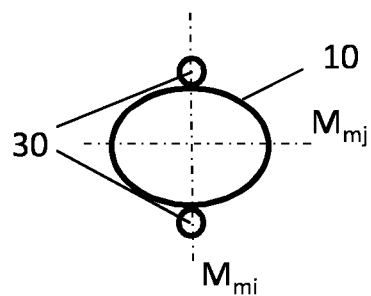

NEEDLE-SUTURE COMBINATION

The present invention relates to a needle-suture combination.

U.S. Pat. No. 5,865,836 discloses a needle-suture combination. This needle-suture combination comprises a surgical needle and a suture. The surgical needle has a pointed tip at each of the two ends and a lateral suture receiving aperture disposed between the two ends. The suture is attached to the needle and comprises a first suture portion and a second suture portion. The first suture portion has a larger pliability than the second suture portion such that the minimal radius of the first suture portion extending from the lateral suture receiving aperture of the needle is relatively small.

In the needle-suture combination of U.S. Pat. No. 5,865,836 the needle is configured to minimize the radius of the suture at the location where the suture is connected to the needle in the lateral suture receiving aperture. Minimization of this radius is desirable as the suture that extends from the longitudinal axis of the needle will increase the cross section area of the needle-suture combination when it is pulled through a pierced tissue opening during use of the needle-suture combination resulting in a larger tissue opening.

The cross section area of the tissue opening that is, after placement of the suture, not filled by the cross section of the suture may be a cause of leakage, for example bleeding when the needle-suture combination is used for suturing blood vessels.

It is an aim of the present invention to provide a needle-suture combination having a needle with two ends and a suture connection location between the two ends, that prevents or reduces leakage caused by a ratio difference between the tissue opening and the suture, or at least to provide an improved needle-suture combination.

The invention provides a needle-suture combination as claimed in claim 1.

According to the invention a needle-suture combination is provided comprising a needle, a suture, and a connection part between the suture and the needle. The connection part of the suture comprises a small cross section area compared with the suture and the connection part has a length which is larger than a longest distance from the suture location connection to each of the ends of the needle.

As a result, the maximal cross section area of the combination of the needle and the connection part, i.e. the maximum cross section area pulled through a tissue opening will be smaller than the cross section area of the combination of the suture and the needle. When a tissue to be sutured is pierced by the needle and the needle and suture are pulled through the tissue opening, the connection part of the suture and the needle are pulled simultaneously through the tissue opening as a result of which the tissue opening will be enlarged to the cross section area of this combination to let it pass.

Thereafter, the tissue opening will only be filled by the cross section area of the suture. Since the maximum cross section area pulled through the tissue opening is smaller than the combination of the cross section areas of the needle and the suture, the placement of the suture is less traumatic.

Thus, by providing a connection part with a smaller cross section area, the ratio between the combined cross section area of the needle and the connection part of the suture compared with the cross section area of the suture can be reduced. As a result of this smaller ratio, the open cross section of the tissue opening not occupied by the suture can be decreased. This has an advantageous effect to prevent or reduce bleeding through this open cross section.

Furthermore, since instead of the suture the connection part will be next to the needle when the needle is pulled through the tissue opening, the cross section area of the suture can be increased to further decrease the ratio between the combined cross section of the needle and the connection part and the cross section of the suture in order to further reduce bleeding, or more generally leakage, through the tissue opening when the suture is placed in the tissue opening.

It is further remarked that tissue usually has some flexibility, so that the tissue opening will be stretched when the largest cross section area of the needle-suture combination, i.e. the combination of connection part and needle is pulled through the tissue opening.

In this application, a cross section of an element means the cross section of the respective element perpendicular to a longitudinal axis of that element. For example, a cross section of the needle is a cross section in a plane perpendicular to the longitudinal axis of the needle. A cross section area is the size of the surface area of the cross section.

A needle-suture combination having a needle with two ends and a suture connection location between the two ends is in particular suitable for use in a surgical suture instrument in which the needle is passed between two jaw elements of the instrument. Such surgical instrument is for example disclosed in WO2013/032329A1, the contents of which are herein incorporated by reference. The needle-suture combination may however also be applied in any other suture technique or instrument in which the use of a needle with two ends and a suture connection location between the two ends is desirable.

In an embodiment, in particular for use in a surgical suture instrument in which the needle is passed between two jaw elements of the instrument, each of the ends of the needle is a holding end configured to be held by the apparatus, such that the needle can be passed forwards and backwards between the two jaw elements.

In an embodiment, the needle comprises a pointed tip at each of its two ends so that the needle can be pierced through tissue in two directions. Alternatively, the needle may comprise one end with a pointed tip and the other end may be blunt. The latter embodiment may for example be used to pass the needle backwards and forwards between two jaw elements of a surgical suture instrument, wherein the needle is only used to pierce through tissue in a single direction.

In an embodiment, the connection part cross section area is equal to or less than 0.5 times the suture cross section area, preferably equal to or less than 0.25 times.

In an embodiment, the suture connection location is arranged substantially midway of the needle. In this way a symmetric design of the needle is obtained which may be advantageous for use of the needle-suture combination in a surgical instrument configured to pass the needle forwards and backwards between two clamping jaws.

The connection part may have a substantially constant cross section area over its length, but this cross section area may also vary over the length of the connection part. Similarly the suture cross section area is substantially constant over the length of the suture, but may also vary. A transition part may be provided between the connection part and the suture to gradually increase the cross section area from the connection part cross section area to the suture cross section area. The transition part may be part of the connection part, the suture, or may be a separate element.

The connection part normally extends over a limited length of at least the distance between the suture connection location and each of the ends of the needle. The suture that is used for the actual applied sutures will typically extend over a substantially longer distance.

In an embodiment, a maximum combined transverse dimension of the needle and the connection part, when arranged next to each other, for example when pulled through a tissue opening created by the needle is 1 to 4 times a maximum transverse dimension of the suture, preferably 1.25 to 2.5 times the maximum transverse dimension of the suture. In such embodiment, the maximum needle transverse dimension may be at least 0.4 times, preferably at least 0.6 times the maximum transverse dimension of the suture.

In an embodiment, the connection part cross section area is substantially circular and has a connection part diameter, and the suture cross section area is substantially circular and has a suture diameter. To optimize the filling of the pierced tissue opening by the suture, the suture may have a circular cross section. In a circular cross section, the transverse dimension is the diameter of the cross section.

In an alternative embodiment, the connection part may at least partly have a non-circular cross section. For example, the side of the connection part that abuts against the needle surface when the needle and the connection part are simultaneously pulled through a tissue opening may be flattened to optimize the combined cross section of the needle and the connection part. In such embodiment, the cross section may be semi-cylindrical having a flat side to abut against the needle surface. In another embodiment, the shape of the cross section of the connection part may be configured to mate with the surface of the needle.

In an embodiment, a maximum cross section area of the needle comprises a circular cross section defining a maximum needle diameter. To minimize damage to the tissue when the needle is pierced into and pulled through the tissue to form a tissue opening, the needle may have a substantial circular cross section over its length, whereby the diameter of the cross section may vary.

The maximum cross section area of the needle is that cross section area perpendicular to the longitudinal axis of the needle having the largest surface area. In case of a circular cross section are, this maximum cross section area is the cross section having the largest diameter.

In another embodiment, a shape of the connection part cross section and a shape of the needle cross section are selected such that when the connection part and the needle are held next to each other a combined cross section thereof substantially corresponds or at least approaches a circular shape.

For example, a needle cross section may have an ellipse shape having a major axis and a minor axis, wherein the connection part, when pulled together with a needle through the tissue opening will be arranged aligned with the minor axis to approach this cylindrical shape.

Advantageously the needle may comprise a narrowing of the needle at the suture connection location to accommodate for a bending curve of the connection part of the suture without extending unnecessarily far from the longitudinal axis of the needle. The cross section of the narrowing may have another shape than circular to maximize the available space for the bending curve of the connection part.

In an embodiment, a sum of the connection part diameter and the maximum needle diameter is 1 to 4 times the suture diameter, preferably 1.25 to 2.5 times the suture diameter.

In an embodiment, the connection part has a length of less than once, preferably less than three quarters of the length of the needle.

In an embodiment, the suture connection location comprises at least one through-going opening through the needle, wherein the connection part runs through the through-going opening.

In an embodiment, the through-going opening comprises at least one channel. The cross section of the through-going opening may correspond to or be slightly larger than a cross section of the part of the connection part running through the through-going opening.

In an embodiment, the through-going opening is a slot running in longitudinal direction of the needle. The slot may extend over a substantial part of the length of the needle, for example at least 40%, preferably at least 60% of the length of the needle. In such embodiment, the connection part may move from one end of the slot to the other end of the slot in dependence of the direction in which the needle is pulled through a tissue opening. This has an advantage that the maximum cross section of the needle and connection part extends over a smaller part of the length of the needle. Furthermore, since the slot extends over a substantial length of the needle, the length of the connection part may be decreased. This also decreases the risk that the connection part will be entangled with other parts of the needle-suture combination, and/or that the connection part will be caught by other elements along which the needle-suture combination is moved.

In an embodiment, the connection part comprises a loop of thread that runs through the through-going opening, wherein loop parts extending from both ends of the through-going opening are each connected to the suture.

The connection part may be a loop of thread that runs through at least one through-going opening in the needle. Such loop may comprise two loop ends that for example both may be connected to the suture. In such embodiment, the first end of the connection part which is used to connect the connection part to the suture connection location of the needle, is formed by a part of the loop of thread running through the through-going opening of the needle. The second end of the connection part, that is used to connect the connection part to the suture is formed by the two loop ends that are connected to the suture.

The through-going opening may have rounded channel ends to allow the loop of thread to bend gradually without requiring the connection part to extend from the needle in radial direction. Furthermore, the loop is prevented by these rounded channel ends from overbending, i.e. bending with a too small radius which may, in dependency of the used materials result in damage of the connection part.

In an embodiment, a part of the loop of thread, or more generally a part of the connection part, running through the through-going opening is fixed in a revolving bearing.

Instead of the connection part running through a channel or slot, a revolving bearing may be provided in which the connection part is fixed. A revolving bearing is a bearing that allows the connection part to change orientation between at least a first orientation direction, in which the connection parts runs from the suture connection location to the first end of the needle, and a second orientation direction, in which the connection parts runs from the suture connection location to the second end of the needle.

By providing a bearing this change in orientation towards the first or second end does not have to be compensated by the connection part itself. This may increase durability of the connection between the connection part and the needle.

The revolving bearing may for example be formed by a tube that can rotate within a cylindrical hole in the needle, whereby the connection part is fixed in the tube.

The bearing allows the connection part to correctly align with the needle, when the needle is pulled in either direction through a tissue opening.

The loop of thread may be pre-shaped to a desired shape.

In an embodiment, the connection part is made of resilient material, wherein the connection part preferably comprises two connection arms each comprising one arm end connected to the suture, wherein the other ends of the connection arms are connected to each other by a bridging element that extends through the through-going opening.

Such resilient material may have a stress-free state to which the connection part will return when no force is exerted on the connection part. The advantage of such connection part is that the position of the connection part is very reliable, and the chance that the connection arms may be entangled with the needle is very small.

The bridging element may form the first end of the connection part, and the arm ends opposite to the connection to the bridging element may form the second end of the connection part.

It is remarked that these arm ends forming the second ends may each separately be connected to the suture, but also first may join to a single joint arm end that is connected to the suture.

The resilient connection part, i.e. the connection part made of resilient material, may for example be made of stainless steel.

It is remarked that the connection part may also be formed by a rigid element. Such rigid element may also comprise two connection arms each comprising one arm end connected to the suture, wherein the other ends of the connection arms are connected to each other by a bridging element that extends through the through-going opening.

In an embodiment, the suture connection location comprises a first opening through the needle in a first direction and a second channel through the needle in a second direction, wherein the first and second direction are non-parallel with respect to each other in a direction substantially perpendicular to the longitudinal direction of the needle.

The advantage of the presence of the first and second channel being arranged non-parallel with respect to each other in a direction substantially perpendicular to the longitudinal direction of the needle, is that when the two loop thread ends running from the suture to the suture connection location do not run at opposite ends of the needle resulting in a combined smaller maximum transverse dimension, i.e. dimension in a direction perpendicular to the longitudinal direction, when compared to the loop threads being at opposite sides of the needle.

In such embodiment, the first direction and the second direction may be substantially perpendicular to a longitudinal direction of the needle. Furthermore, the first direction and the second direction may be substantially perpendicular to each other in the direction substantially perpendicular to the longitudinal direction of the needle.

In an embodiment, the suture connection location comprises a first opening in or through the needle, wherein the first end of the connection part is attached to the needle in the first channel. This attachment to the needle may be carried out in any suitable way such as clamping, gluing, melting, welding etc.

In an embodiment, the suture and the connection part are connected to each other with a transition part which gradually increases in cross section from the connection part cross section to the suture cross section. Such transition part prevents the presence of rims or such that may get caught by elements along which the needle-suture location is moved.

In an embodiment, the needle is a straight needle or a curved needle. Dependent on the application it may be desirable to use a curved or a straight needle. The needle-suture combination of the present invention may have either a straight needle or a curved needle.

In an embodiment, the suture cross section area is in the range of $0.002$ mm$^2$ to $0.3$ mm$^2$. In case the suture comprises a cylindrical cross section, the diameter of this cross section may for example be in the range of 0.05 mm to 0.6 mm; For instance, the suture diameter may be about 0.1 mm, about 0.15 mm, or about 0.2 mm.

In an embodiment, a maximum cross section area of the needle is in the range of $0.008$ mm$^2$ to $0.3$ mm$^2$. In case, the maximum cross section area of the needle has a cylindrical cross section, the maximal needle diameter of this cross section may be in the range of 0.1 mm to 0.6 mm.

To optimize an atraumatic effect of the needle-suture combination, i.e. the suture substantially prevents leakage through a tissue opening that is pierced with a maximum combined cross section area of the needle and the connection part, it is desirable that the suture cross section area is relatively large compared with the maximum combined cross section area.

When the tissue will be stretched out when the maximum combined cross section area of needle and connection part is pulled through the tissue opening, it may be desirable to have a suture cross section area smaller than the maximum combined cross section area of needle and connection part. This facilitates pulling the suture through the tissue opening. For example, the suture cross section area is maximally 90% of the maximum combined cross section area.

In an embodiment, the suture and needle generally have a cylindrical cross section of which the diameter may vary over their respective lengths, the maximum needle diameter may be about 0.3 mm, the suture diameter about 0.15 and the connection part diameter may be about 0.05 mm.

In an embodiment, the needle comprises a non-circular cross section, preferably an ellipse cross section, having a major dimension and a minor dimension, and wherein, when the needle-suture combination is configured to arrange the connection part in line with the minor dimension of the non-circular cross section. For example, the needle may have an ellipse cross section having a major axis and a minor axis, wherein the connection part is configured to be arranged at the minor axis when the needle-suture combination is pulled through a tissue opening. The ratio between the major axis and the minor axis may for example be 3:2, for instance about 0.3 mm in the major axis and 0.2 mm in the minor axis.

It will however be clear that many more combinations of cross section areas for needle, suture and connection part may be used.

Further characteristics and advantages of the invention will now be elucidated by the description of four embodiments of the inventions, whereby reference is made to the accompanying drawings in which.

Figure 4:
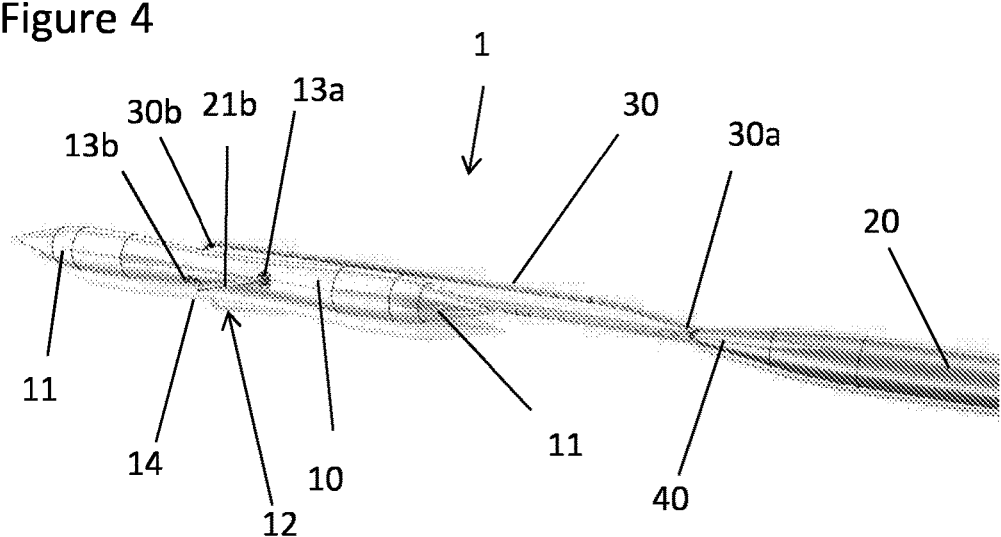
Figure 5:
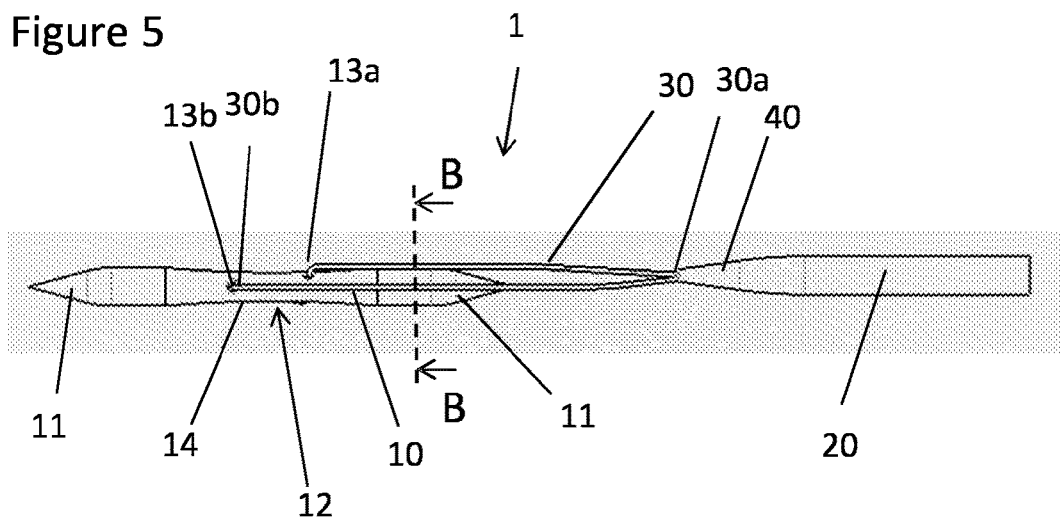
Figure 6:
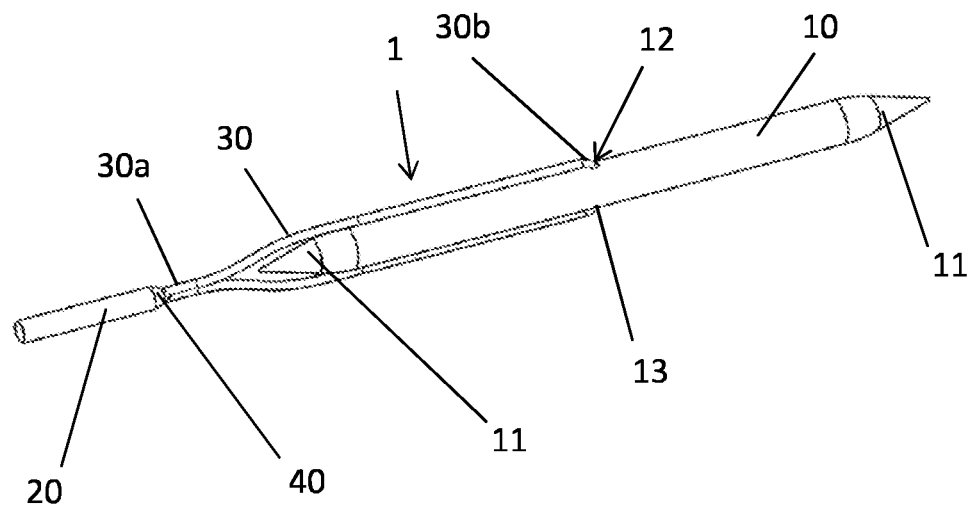
Figure 7:
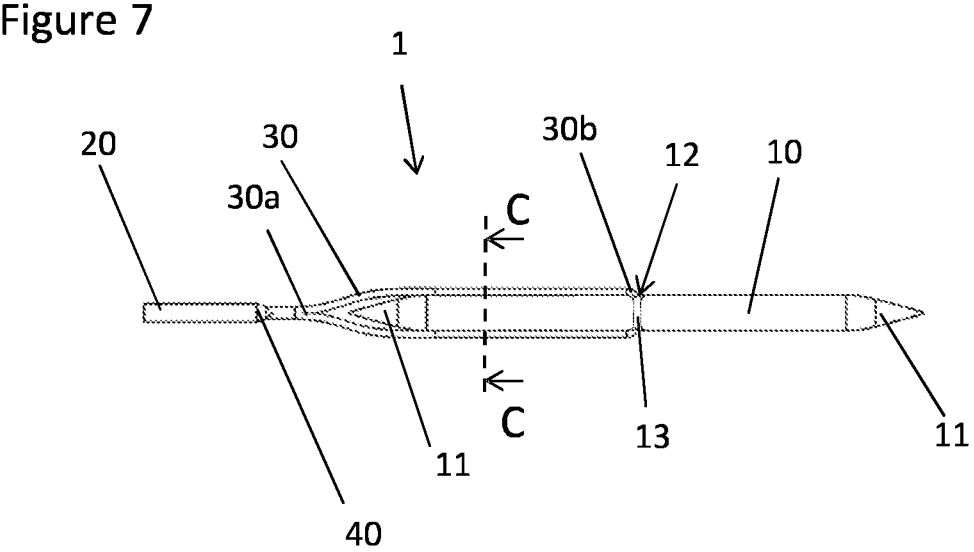

FIG. 3*a*-3*f* show different embodiments of adjacent cross sections of the connection part and the needle in side view;

FIG. 4 shows a perspective view of a needle-suture combination according to a second embodiment of the invention;

FIG. 5 shows a top view on the needle-suture combination of FIG. 4;

FIG. 6 shows a perspective view of a needle-suture combination according to a third embodiment of the invention;

FIG. 7 shows a side view on the needle-suture combination of FIG. 6

Figure 8:
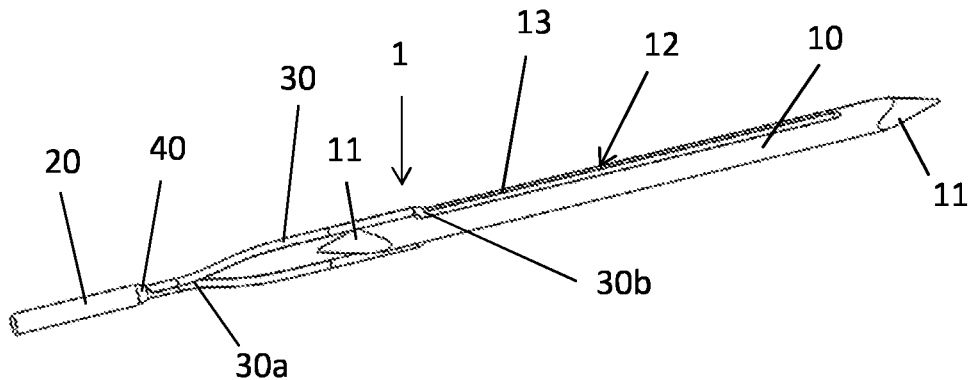
Figure 9:
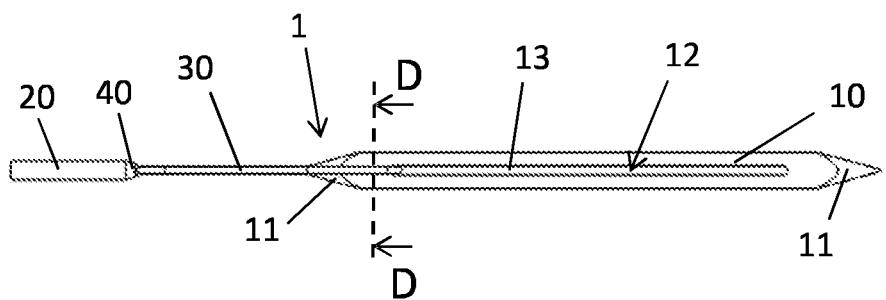
Figure 10:
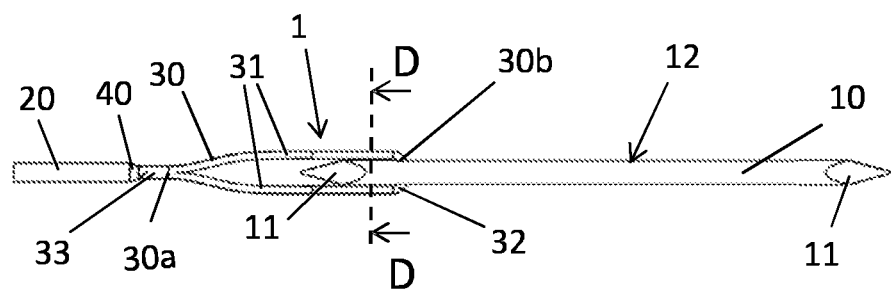

FIG. 8 shows a perspective view of a needle-suture combination according to a fourth embodiment of the invention; and FIG. 9 shows a top view on the needle-suture combination of FIG. 8; and FIG. 10 shows a side view on the needle-suture combination of FIG. 8.

Figure 1:
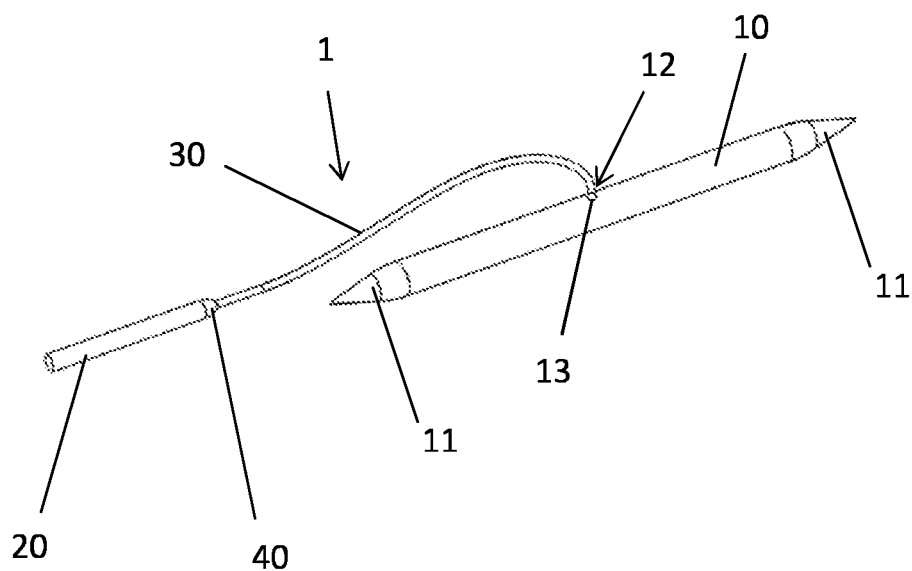
FIG. 1 shows a perspective view of a needle-suture combination according to a first embodiment of the invention.
Figure 2:
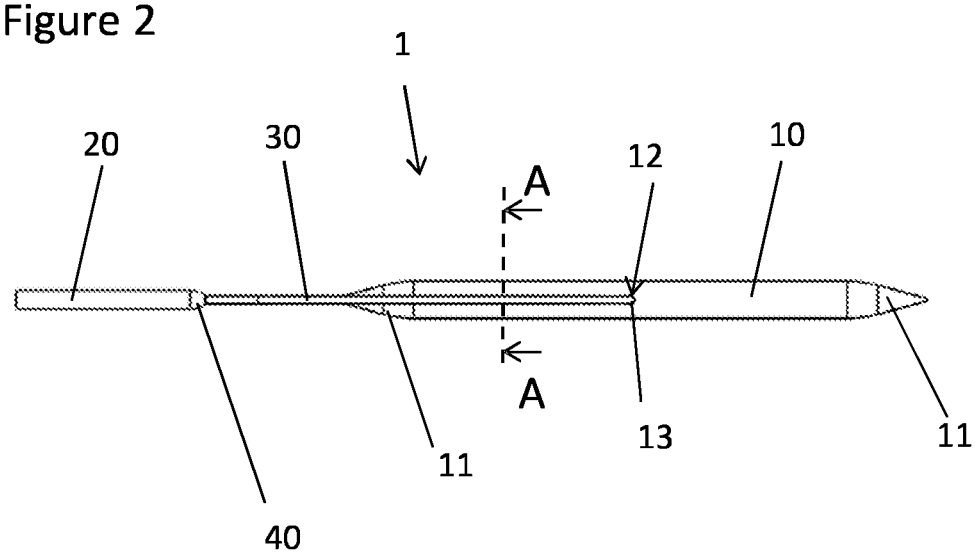
FIG. 2 shows a top view on the needle-suture combination of FIG. 1.

FIG. 1 shows a perspective view of a first embodiment of a needle-suture combination according to the invention, generally indicated by the reference numeral 1. The needle-suture combination 1 comprises a needle 10, a suture 20 and a connection part 30. FIG. 2 shows a top view on the needle-suture combination of FIG. 1.

The needle 10 is a substantially straight needle 10 having a elongate shape with a substantially circular cross section. At each of the opposite ends of the needle 10 a pointed tip 11 is provided which tip is configured to be pierced through tissue to be sutured.

Substantially halfway the needle 10, a suture connection location 12 is provided for connection of the suture 20 to the needle 10. To connect the suture 20 to the needle 10, the connection part 30 is used. The suture connection location 12 comprises a lateral aperture 13 through which the first end of the connection part 30 can be placed and attached, for example by clamping, gluing, melting, welding or any other suitable method. Similarly, the second end of the connection part 30 may be connected to the suture 20.

The needle 10 comprises a circular cross section over the length of the needle 10. In an alternative embodiment, the needle cross section area of a middle region of the needle 10 may be smaller than the outer ends of the needle 10 such that at the suture connection location 12 a narrowing of the needle is created. The advantage of such narrowing may be that the suture part that extends from the aperture 13 extends less from the longitudinal axis of the needle 10 when the suture is bent in its minimal radius along the needle.

The needle 10 is designed for use in a surgical instrument in which the needle may be passed between two jaws of the instrument. Such surgical instrument is for example disclosed in WO2013/032329A1, the contents of which are herein incorporated by reference.

The needle 10 may also be used in any other suitable application, and may for instance be used in a surgical procedure in which the needle is manipulated by using conventional surgical instruments.

The maximum needle diameter is for example in the range of 0.1 to 0.6 mm, preferably in the range of 0.2 mm to 0.5 mm.

The length of the needle 10 may be in the range of 2 mm to 12 mm, preferably 5 mm to 9 mm.

The needle 10 may be made of any suitable type of material, such as stainless steel, tungsten and its alloys, ceramics or polymer materials. The material may for example be stainless steel AISI 420, Tungsten Rhenium W25Re, Zirconium oxide ZrO2 (TZP), or carbon reinforced polyetheretherketone (PEEK CF).

The suture 20 and the connection part 30 are connected to each other by a transition part 40. The suture 20 is the actual suture material that will remain in the body after the suture has been finished.

The connection part 30 and the suture 20 each have a circular cross section, whereby a connection part diameter of the connection part 30 is substantially smaller than a main part diameter of the suture 20. The transition part 40 widens from the connection part diameter to the main part diameter to provide a smooth transition between the connection part 30 and the suture 20.

The suture 20, the connection part 30 and the transition part 40 may be made of the same material or from different materials. These materials may be monofilaments or multifilaments or other suitable suture materials. The transition part 40 may also be made of metal, polymer or ceramics materials.

In an embodiment, the suture 20 may be made of prolene, and the connection part 30 may be made of stainless steel.

The suture 20 may have a diameter in the range of 0.01 mm to 0.6 mm.

In the embodiment as shown in FIGS. 1 and 2, the needle diameter is about 0.3 mm, the connection part diameter of the connection part 30 is about 0.05 mm and the suture diameter of the suture 20 is 0.15 mm.

In accordance with the invention, the diameter of the connection part is smaller than the diameter of the main part. Furthermore, in the shown embodiment, the length of the connection part 30 is approximately the same as the length of the needle 10 such that when the suture 20 extends along the needle 10, only the connection part 30 is arranged against the needle surface, while the suture 20 is arranged in line with the needle 10 when the suture 20 is pulled straight from the suture connection location 12. In practice, the length of the connection part 30 may for example be reduced to 0.6 times the needle length.

As a result, the maximum transverse dimension of the combination of needle 10 and the connection part 30, i.e. at the line A-A, is 0.35 mm. This transverse dimension of 0.35 mm is only approximately 2.3 times the transverse dimension of the suture 20, while when the connection part 30 would have the same diameter as the suture 20 the maximum transverse dimension of the combination of needle 10 and connection part of the suture 20 would be approximately 3 times the diameter of the suture 20.

The reduced maximum transverse dimension of the combination of the suture 20 and the needle 10 at the line A-A when the suture 20 extends along the needle 10 reduces the size of the tissue opening that is pierced in a tissue to be sutured when using the needle-suture combination 1. At the same time, the diameter of the suture 20 which remains in the tissue opening does not have a reduced size. As a result, less surface area of the tissue opening remains open after final placement of the suture and there is less risk on bleeding through the tissue opening, or at least a reduced amount of blood may pass through the tissue opening.

FIG. 3a shows a cross section of the embodiment of FIGS. 1 and 2, where the connection part 30 of the suture 20 and the needle are arranged against each other. When the needle-suture combination is pulled through a tissue opening created with the needle, the cross section of FIG. 3a is the largest cross section that will occupy the tissue opening. In dashed lines the cross section of the suture 20 is shown. It is clear that the maximum diameter is substantially reduced as a result of the reduced diameter of the suture at the connection part 30. It will be clear that such reduction may have a substantial positive effect on the prevention or decrease of bleeding through the tissue opening after placement of a suture in the tissue.

FIG. 3b shows an alternative embodiment of a cross section of the connection part 30. In this embodiment, the cross section of the connection part 30 is flattened at the side of the needle 10 to further optimize the space in practice occupied by the connection part and the needle 10.

FIG. 3c shows a further optimized embodiment in which the shape of the side of the connection part 10 that abuts against the needle 10, when the needle-suture combination 1 is pulled through the tissue opening, is configured to mate with the surface of the needle 10. In other words, the side of the connection part 30 that lies against the needle is given an inverse shape of the needle surface so that the two surfaces abut against each other.

FIG. 3d, also shown in FIGS. 4 and 5, shows yet another embodiment of a needle-suture combination. In this embodiment, the connection part 30 comprises two loop threads that are arranged at an angle of approximately 90 degrees with respect to the cross section of the needle 1. This has the advantage that the two loop threads are not arranged at opposite sides of the needle 10 which reduces the maximum transverse dimensions of the combination of the needle 10 and the connection part 30.

FIGS. 3e and 3f show a cross section C-C of a third embodiment, also shown in FIGS. 6 and 7, and a cross section D-D of a fourth embodiment, also shown in FIGS. 8, 9 and 10.

In the third embodiment, shown in FIG. 3e, the needle cross section is circular and the connection part 30 comprises two loop arms extending at opposite sides of the needle. As the sum of diameters of the two loop arms is substantially smaller than the diameter of the suture, the combined diameter of the needle and the connection part 30, i.e. the combination of the two loop arms, is smaller than the combination of the needle diameter and the suture diameter.

In the fourth embodiment shown in FIG. 3f, the needle cross section has an ellipse shape having a major axis $A_{mj}$ and a minor axis $A_{mi}$. The diameter of the major axis $A_{mj}$ is for example 0.3 mm and the diameter of the minor axis $A_{mi}$ may be 0.2 mm. The diameter of the loop arms of the connection part 30 may be 0.05 mm.

The connection part 30, in particular the loop arms at opposite sides of the needle, are configured and arranged to extend, when pulled together with a needle through a tissue opening, adjacent to and in parallel the needle and on the minor axis $A_{mi}$. As a result, the combined dimension of needle 10 and connection part 30 in the direction of the minor axis $A_{mi}$ is 0.3 mm which corresponds with the diameter of the needle cross section in the direction of the major axis $A_{mj}$. The combination of the needle 10 and connection part 30 approaches a cylindrical shape of a needle having a diameter of 0.3 mm.

FIGS. 4 and 5 show a perspective and top view of the needle-suture combination 1 of FIG. 3d. The same elements of this needle-suture combination 1 or elements having substantially the same function as the elements of the needle-suture combination 1 of FIGS. 1 and 2 have been given the same reference numerals.

The needle 10 is a straight needle having an elongate shape with a substantially circular cross section. At each of the opposite ends of the needle 10 a pointed tip 11 is provided which tip is configured to be pierced through tissue to be sutured to form a tissue opening through which a suture 20 is led.

Halfway the needle 10, a suture connection location 12 is provided to connect the suture 20 to the needle 10. The suture connection location 12 is arranged in a narrowing 14 of the needle 10, i.e. a region of the needle which has a smaller cross section area than the maximum cross section area of the needle 10.

A connection part 30 is provided to connect the suture 20 to the needle 10, wherein a first end of the connection part 30 is connected to the needle 10 and a second end of the connection part 30 is connected to the suture 20 via a transition part 40. The transition part 40 provides a smooth transition in diameter between the connection part 30 and the suture 20.

The connection part 30 is a loop of thread having a substantially smaller diameter than the diameter of the suture 20.

The suture connection location 12 comprises a first channel 13a and a second channel 13b through the body of the needle. The first channel 13a and the second channel 13b are arranged in two parallel planes perpendicular to the longitudinal axis of the needle 10. Furthermore, the first channel 13a and the second channel 13b are arranged in the direction perpendicular to the longitudinal axis at an angle of 90 degrees with respect to each other. As a result of the first channel 13a and the second channel 13b running in these directions, the loop threads of the connection part 30 are arranged at an angle of approximately 90 degrees in the cross section B-B.

It is remarked that at the location of the first channel 13a and second channel 13b, respectively, the loop threads are positioned at diametrically opposed sides of the needle 10, but these locations are arranged in the narrowing 14 of the needle 10 and thus have less effect on the maximum transverse dimension of the combination of needle 10 and connection part 30 when pulled through a tissue opening.

The materials and sizes of the needle 10 and suture 20 may be the same as described with respect to the embodiment of FIGS. 1 and 2.

The connection part 30 comprises a first end that is connected to the needle 10 at the suture connection location 12 and a second end that is connected to the suture 20. In the embodiment of FIGS. 4 and 5, two loop ends 30a of the loop of thread together form the second end of the connection part 30. The first end of the connection part 30 is formed by a part 30b of the loop of thread that runs through the needle 10.

FIGS. 6 and 7 show a third embodiment of a needle-suture combination according to the invention in perspective and side view, respectively.

The connection part 30 comprises a loop of thread. The two loop ends 30a are connected via the transition part 40 to the suture 20 to form a second end of the connection part 30. The first end of the connection part 30 is formed by a middle part 30b of the loop of thread.

The loop of thread may be formed by a flexible thread, for example a stainless steel flexible thread. The loop of thread may also be pre-shaped to the shape shown in FIGS. 6 and 7. The loop of thread runs through the channel 13 from one side of the needle 10 to the other side of the needle 10. The channel ends of the channel are rounded as shown in dashed lines to allow the loop of thread to bend gradually without requiring the connection part 13 to extending from the needle in radial direction. In this way, the loop of thread is prevented from overbending, i.e. bending with a too small radius, which may, in dependency of the used materials result in damage of the connection part 13.

The dimensions and materials of the suture needle combination of FIGS. 6 and 7 may correspond to the other embodiments discussed above.

It is remarked that the loop of thread may be fixed in a revolving bearing for instance a tube like element that may rotate in a cylindrical channel provided in the needle. Such revolving bearing may increase the durability of the connection part 30.

FIGS. 8, 9 and 10 show a fourth embodiment of a needle-suture combination according to the invention in perspective, top view and side view, respectively. There are three major differences between the third embodiment and the fourth embodiment. The first difference is that the cross section of the needle 10 of the fourth embodiment is ellipse shaped as discussed above with reference to FIG. 3f. However, in an alternative embodiment, the cross section of the needle 10 may also be cylindrical.

The second difference is that the through-going opening of the fourth embodiment is formed as a slot 13 extending over a substantial part of the length of the needle 10. The connection part 30 may move from one end of the slot 13 to the other end of the slot 13 in dependency of the direction in which the needle 10 is pulled, for example through a tissue opening. This has an advantage that the maximum cross section of the needle 10 and the connection part 30 extends over a smaller part of the length of the needle, when the needle 10 is pulled with the connection part 30 through a tissue opening.

The third difference between the third embodiment and the fourth embodiment is that the connection part 30 of the fourth embodiment is made of resilient material. Such resilient material may have a stress-free state to which the connection part 30 will return when no force is exerted on the connection part 30. This stress free state is shown in FIGS. 8, 9 and 10. The advantage of the resilient connection part 30 is that the shape and position of the connection part 30, when pulled through a tissue opening is very reliable. As a result, the chance that the connection part 30 may be entangled with the needle 10 is very small.

The connection part 30 comprises two connection arms 31 each comprising one arm end connected to the suture 20. The other ends of the connection arms 31 are connected to each other by a bridging element 32 that extends through the slot 13.

The bridging element 32 forms the first end 30a of the connection part 30, and the arm ends opposite to the connection to the bridging element may form the second end of the connection part. The arm ends forming the second end join together in part 33 before the connection part 30 is connected to the suture 20 by the transition part 40.

The resilient connection part 30 may for example be made of stainless steel.

It is remarked that the connection part 30 of the third embodiment may be replaced by the resilient connection part 30 of the fourth embodiment, but also the resilient connection part 30 of the fourth embodiment may be replaced by a loop of thread.

The invention claimed is:

1. A needle-suture combination, comprising:
a surgical needle having a main body with two ends and a suture connection location arranged in the main body between the two ends;
a suture; and
a connection part,
wherein a first end of said connection part is connected to the needle at the suture connection location and an opposite second end of the connection part is connected to the suture,
wherein the connection part comprises a connection part cross section area and the suture comprises a suture cross section area,
wherein the connection part cross section area is smaller than the suture cross section area,
wherein the connection part has a length which is larger than a longest distance from the suture connection location to each of the two ends of the needle,
wherein the suture connection location comprises at least one through-going opening through the main body of the needle from one side of the needle to an other side of the needle, and
wherein the connection part comprises a loop of thread that runs through the through-going opening, wherein loop parts extending from both ends of the through-going opening are each connected to the suture.

2. The needle-suture combination of claim 1, wherein the connection part cross section area is equal to or less than 0.5 times the suture cross section area.

3. The needle-suture combination of claim 1, wherein a maximum combined transverse dimension of the needle and the connection part, when arranged next to each other is 1 to 4 times a maximum transverse dimension of the suture.

4. The needle-suture combination of claim 1, wherein the connection part cross section area is substantially circular and has a connection part diameter, and wherein the suture cross section area is substantially circular and has a suture diameter.

5. The needle-suture combination of claim 4, wherein a sum of the connection part diameter and the maximum needle diameter is 1 to 4 times the suture diameter.

6. The needle-suture combination of claim 1, wherein a maximum cross section area of the needle comprises a circular cross section defining a maximum needle diameter.

7. The needle-suture combination of claim 1, wherein the connection part has a length of maximally once a length of the needle.

8. The needle-suture combination of claim 1, wherein the through-going opening comprises at least one channel.

9. The needle-suture combination of claim 1, wherein the through-going opening is a slot running in longitudinal direction of the needle.

10. The needle-suture combination of claim 1, wherein the connection part is made of resilient material, and wherein the connection part comprises two connection arms each comprising one arm end connected to the suture, wherein the other ends of the connection arms are connected to each other by a bridging element that extends through the through-going opening.

11. The needle-suture combination of claim 1, wherein the suture connection location comprises a first channel through the needle in a first direction and a second channel through the needle in a second direction, wherein the first direction and the second direction are non-parallel with respect to each other in a direction substantially perpendicular to the longitudinal direction of the needle, and wherein the loop of thread runs through the first channel and the second channel.

12. The needle-suture combination of claim 1, wherein the suture and the connection part are connected to each other with a transition part which gradually increases in cross section from the connection part cross section to the suture cross section.

13. The needle-suture combination of claim 1, wherein the needle is a straight needle.

14. The needle-suture combination of claim 1, wherein the needle comprises a non-circular cross section having a major dimension and a minor dimension, and wherein the needle-suture combination is configured to arrange the connection part in line with the minor dimension of the non-circular cross section.

15. The needle-suture combination of claim 1, wherein the needle comprises a pointed tip at each of the two ends.

16. The needle-suture combination of claim 1, wherein the connection part cross section area is equal to or less than 0.25 times the suture cross section area.

17. The needle-suture combination of claim 1, wherein a maximum combined transverse dimension of the needle and the connection part, when arranged next to each other is 1.25 to 2.5 times the maximum transverse dimension of the suture.

18. The needle-suture combination of claim 1, wherein the through-going opening is formed by a channel having rounded channel ends.

19. The needle-suture combination of claim 1, wherein the loop of thread is pre-shaped to a desired shape.

* * * * *